United States Patent [19]

Wojcicki et al.

[11] Patent Number: 5,190,522
[45] Date of Patent: Mar. 2, 1993

[54] DEVICE FOR MONITORING THE OPERATION OF A DELIVERY SYSTEM AND THE METHOD OF USE THEREOF

[75] Inventors: Jan Wojcicki, Warsaw; Boguslaw Lilpop, Pruszhow; Marek Ziembicki; Stanislaw Bielawski, both of Warsaw, all of Poland

[73] Assignees: Institute of Biocybernetics and Biomedical Engineering P.A.S., Warsaw, Poland; Novo Nordisk A/S, Bagsvaerd, Denmark

[21] Appl. No.: 745,988

[22] Filed: Apr. 11, 1991

Related U.S. Application Data

[63] Continuation-in-part of Ser. No. 639,657, Jan. 11, 1991, abandoned, which is a continuation-in-part of Ser. No. 467,613, Jan. 19, 1990, abandoned.

[30] Foreign Application Priority Data

Jan. 20, 1989 [PL] Poland .................................. 277308

[51] Int. Cl.[5] ............................................. A61M 5/20
[52] U.S. Cl. ........................................ 604/65; 604/31; 604/118; 128/DIG. 12
[58] Field of Search ............... 604/118, 245, 65, 66, 604/67, 30, 31, 151, 152, 153, 154, 6; 128/DIG. 12, DIG. 13

[56] References Cited

U.S. PATENT DOCUMENTS

| | | | |
|---|---|---|---|
| 4,551,133 | 11/1985 | de Beyl et al. | 604/66 |
| 4,657,529 | 11/1985 | Prince et al. | 604/6 |
| 4,710,164 | 12/1987 | Levin et al. | 604/66 |
| 4,718,891 | 1/1988 | Lipps | 604/31 |
| 4,758,228 | 7/1988 | Williams | 604/153 |
| 4,762,518 | 8/1986 | Kreineck | 604/245 |
| 4,871,351 | 10/1989 | Feingold | 604/65 |
| 4,898,576 | 2/1990 | Philip | 604/65 X |
| 5,006,997 | 4/1991 | Reich | 604/31 X |
| 5,010,473 | 4/1991 | Jacobs | 604/65 X |
| 5,078,682 | 1/1992 | Miki et al. | 604/67 X |

FOREIGN PATENT DOCUMENTS

| | | |
|---|---|---|
| 0040592 | 11/1981 | European Pat. Off. |
| 0291727 | 11/1988 | European Pat. Off. |
| 0296124 | 12/1988 | European Pat. Off. |
| WO84/01719 | 5/1984 | PCT Int'l Appl. |

OTHER PUBLICATIONS

"Ambulatory Insulin Infusion Pumps", *Health Devices*, pp. 351-376 (Nov. 1987).

Prestele et al., "State of Development of Program-Controlled Implantable Insulin Delivery Systems", *Art Sys for Insulin Delivery*, pp. 141-153 (1983).

*Primary Examiner*—John D. Yasko
*Attorney, Agent, or Firm*—Steve T. Zelson; Elias J. Lambiris

[57] ABSTRACT

A device for monitoring a delivery system comprising a volumetric micropump, a measuring element or sensor located in the infusion line, a matching system and an analyzing system. The devices are preferably for use in insulin administration when treating type-I diabetes and in analytical laboratories, the chemical and pharmaceutical industries and other technologies.

8 Claims, 1 Drawing Sheet

DEVICE FOR MONITORING THE OPERATION OF A DELIVERY SYSTEM AND THE METHOD OF USE THEREOF

CROSS-REFERENCE TO RELATED APPLICATIONS

This application is a continuation-in-part of co-pending application Ser. No. 07/639,657 filed on Jan. 11, 1991, now abandoned which is a continuation-in-part of application Ser. No. 07/467,613 filed Jan. 19, 1990, now abandoned. Both applications are incorporated herein by reference.

BACKGROUND OF THE INVENTION

1. Field of the Invention

The present invention relates to a device for monitoring the operation of a drug delivery system, in particular an insulin delivery system, a drug delivery system comprising the device and the method of use of the device.

2. Discussion of the Prior Art

Delivery systems including the device of the present invention are suitable for use not only for medical treatment purposes but also as batch feeders in analytical laboratories, the chemical and pharmaceutical industries and other technologies.

Insulin delivery systems usually provide infusions in two forms: (1) the basal flow rates aimed to cover the daily requirement of insulin of the body and (2) supplementary flow rates meant to compensate for meals. In some constructions, infusions can also be adjusted to account for increased physical activity or for increased demand caused by the "dawn phenomenon".

Insulin is infused in very small amounts on the order of some microliters per hour. For technical reasons, it is very difficult for pumps to deliver such small amounts as a constant flow. Instead, they can be controlled to perform a single pumping cycle delivering on the order of 1 $\mu$l at intervals of several minutes. In connection with meals, pumps may be manually controlled to perform with high frequency a series of pumping cycles as bolus infusions.

Safe operation of a drug delivery system is a fundamental requirement as a malfunction of the system can cause either an overdose of the hormone or a lack of infusion of the hormone which constitute serious hazards to the life of a patient.

Furthermore, devices for monitoring the operation of a drug delivery system should be as compact as possible in order to be easily portable. Therefore, the number of measuring units such as sensors and monitors should be as few as possible.

A number of different constructional solutions of portable and implantable drug delivery systems exist.

Two examples of such systems are the Betatron I TM and II TM (manufactured by Cardiac Pacemakers Inc.). In these systems, the following alarm states are signalled: Supply voltage drop, an empty drug reservoir, blockage of the outlet catheter, microcomputer breakdown, the failure of the internal memory of the system, a too high frequency of the pump operation, a motor breakdown, a dose of insulin in excess of the established daily dose of insulin and erroneous initial data input (improper programming of the infusion). The Betatron I TM and II TM delivery systems are described in *Health Devices*, Nov. 1987, "Ambulatory Insulin Infusion Pumps", pp. 351-376 (in which nine ambulatory insulin infusion pumps are evaluated).

In another construction, MRS-1 TM (manufactured by Disetronic AG/Ltd.), the following alarm states are detected: Electronic systems, the supply battery, the drug level in the reservoir, outlet catheter patency and the administration of an excess dose of insulin in the form of bolus infusions.

In the solutions mentioned above, alarm states such as an empty drug reservoir, a too high frequency of the operation of the pump or a dose of insulin in excess of the daily allowable insulin dose are determined by counting control impulses fed to the pump. Hence, these monitoring systems provide merely indirect monitoring of the correctness of an insulin infusion. This is also true of other alarm states. For instance, monitoring of the operation of the pump (flow control) is carried out by measuring the movement of its mechanical parts.

Clinical applications of insulin delivery systems have indicated that during long-term continuous insulin infusion (especially when implantable systems are used), one of the most frequent technical problems is connected with blockage of the outlet catheter. In order to solve this problem, monitoring of the threshold pressure in the outlet catheter has been used.

An exemplary solution of such monitoring with a view to "catheter plugging" was developed by Siemens and is described in K. Prestele and M. Frentzki, "State of Development of Program-Controlled Implantable Insulin Delivery Systems" in "Artificial Systems for Insulin Delivery" edited by P. Brunetti et al., 1983, Raven Press, New York, pp. 141-153. According to this system, the measurement of the pressure is performed as an indirect non-quantitative check of the flow of insulin through the pump outlet.

This system consists of a non-conducting cylinder having a diameter equal to the inner diameter of the catheter, two electrodes and a unit for measuring the conductivity in the circuit: Electrode—catheter section containing the cylinder—electrode. During normal operation of the pump, overpressure is generated which causes an increase in both the diameter of the catheter and the flow of the insulin (which is a conductor) around the cylinder. A blockage of the catheter results in a much stronger signal than the signal during normal operation. If the pressure threshold value is exceeded by 1 bar the alarm is switched on.

Other examples of technical solutions in which pressure monitoring has been utilized are described below.

U.S. Pat. No. 4,551,133, entitled "Patient Controlled Medication Infusion System" (by Zegers de Beyl), describes a system which is capable of monitoring the physiological conditions of the patient (respiratory and heart rates) by providing a pressure transducer which is in fluid wave pressure communication (placed directly or indirectly—sensor connected to a syringe plunger) with the fluid being infused into the peripheral vein of the patient through an infusion line. This system can also detect the infiltration or occlusion of the infusion line.

The microprocessor used in this system continuously tracks the amplitude of the signal and keeps the amplitude constant using an automatic gain control amplifier. Additionally, (when the pump is not operating) the static pressure is measured in the infusion line. The microprocessor is programmed to measure the amount of gain control which must be applied to the signal during normal operation of the pump and to measure the initial level of static pressure in the infusion line. The microprocessor monitors the physiological conditions of the patient (respiratory rate, heart rate), automatic gain control value and static pressure, by averaging these values over a preselected period of time, such as two minutes, and then comparing them with preselected reference limit values.

When the amount of gain goes beyond a certain threshold toward a maximum, the microprocessor recognizes that the signal has been lost. The loss of the signal indicates the infiltration and/or occlusion of the infusion line. This device can measure, based on two minute intervals, average respiratory and heart rates of the patient as well as check every two minutes whether the infusion line between the pump and the patient is occluded and/or infiltered.

However, the device cannot monitor the operation of a delivery system. This is underlined by the fact that according to Zegers an occlusion of the catheter means loss of signal. On the other hand, as shown below, the device for monitoring the operation of a delivery system according to the present invention will cause a powerful signal in the case of catheter blockage.

In European Patent Application No. 0,296,124, "Pump, Particularly for Enteral Fluid Control, Cassette for Pump, and Method of Operating Pump" (Frantz Medical Development Ltd.), a pressure transducer is used for monitoring three alarm states, (1) an empty cassette receiving chamber, (2) an upstream blockage or occlusion in the supply tube, and (3) a downstream blockage or occlusion such as the patient kinking output tube.

According to Frantz, alarm states are determined by a piezoelectric disc transducer placed between the piston and bellows chamber which detects the pressure inside the pump driving system, i.e., monitoring of the alarm states is determined outside the infusion line. During normal pumping, the piston and transducer remain in contact with the cassette bellows thus producing an electric signal which is comparable to the reference value. In the case of downstream occlusion, the peak of the pressure curve is higher than the peak of the normal voltage signal. This indicates that the piston is encountering more than usual resistance in compressing the bellows. In the case of upstream occlusion, the typical bell curve described by the pressure signal from the transducer is shifted some milliseconds later with respect to the motor cycle and piston movement. Finally, if a cassette is not properly latched into the cassette-receiving chamber, the transducer output signal remains at 0 volts due to the fact that there is no contact between the piston and bellows, and the transducer is not pressurized.

In the prior art systems mentioned above, alarm states are determined by many different methods. These monitoring systems provide merely indirect monitoring of the correctness of a drug infusion, i.e., the measurements concerning the relation between certain parts of the driving system are not directly connected with the state of fluid infusion, and consequently there is no guarantee that the drug is actually introduced into the body of the patient. For example, the prior art devices cannot be used for determining whether the pump is feeding air instead of the drug.

Furthermore, the prior art solutions are all examples of "open-loop" units for continuous monitoring of the operation of portable drug delivery systems, i.e., they cannot use the measurements to correct the operation of the pump.

It is the object of the present invention to provide a device which accurately monitors the operation of a drug delivery system and therefore guarantees that the drug is infused into the body of the patient.

It is also the object of the present invention to provide a device for monitoring the operation of a drug delivery system which is compact and easily portable, i.e., a device which can be used in small portable units to realize long-term continuous drug infusion. It is also the object of the present invention to provide a device which can operate as a closed-loop system.

SUMMARY OF THE INVENTION

The present invention relates to a device for monitoring the operation of a drug delivery system, comprising:

(a) a volumetric micropump which delivers in the form of a single stroke a preset amount of a drug from a drug reservoir through a catheter to a patient body;

(b) a measuring element or sensor located in the infusion line which generates an analog signal based on the actual pressure or the single stroke volume of the micropump;

(c) a matching system which conditions the signal produced by the measuring element or sensor and transmits the signal to a measuring system which measures the peak value and zero level of the signal and transmits the measured parameters to an analog-to-digital converter; and (d) an analyzing and control system which compares the measured parameters and the calculated amplitude with preset values recorded in the memory of the analyzing and control system and which (i) signals an alarm state or automatically corrects the operation of the micropump if a quantitative deviation in the volume of a single stroke of the pump is detected and (ii) signals an alarm state if another alarm state of the drug delivery system is detected.

The present invention also relates to a drug delivery system comprising the device and to a method of using the device.

DETAILED DESCRIPTION OF THE INVENTION

Figure 1:
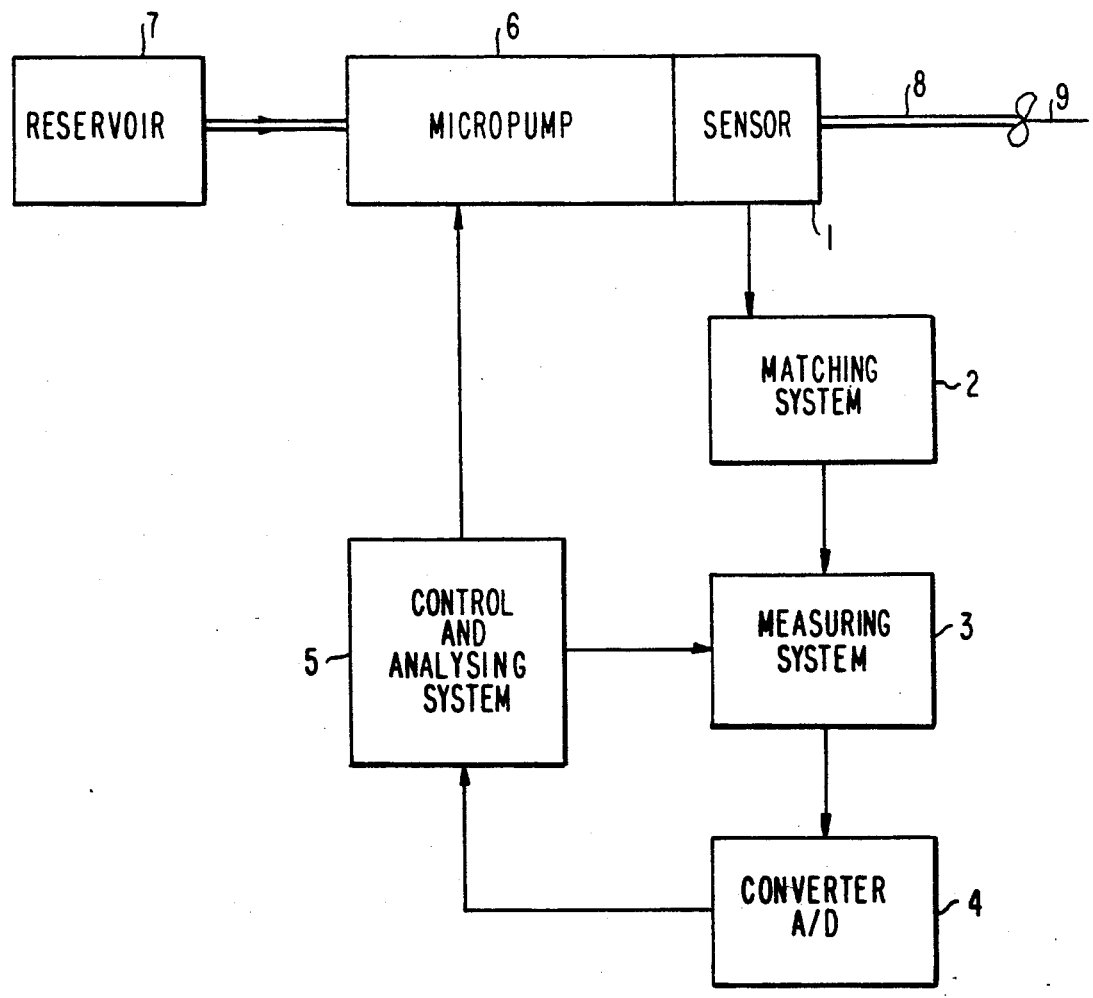
FIG. 1 is a block diagram of a device of the present invention for monitoring the operation of a drug delivery system.

The device of the present invention achieves the above mentioned objects by providing a measuring element or sensor in the infusion line, e.g., between the end of the pump and the inlet of the catheter, which enables the measurement of the actual pressure during the operation of the pump. The measuring element or sensor is therefore located in a position where it enables the measurement of the pressure of each single stroke volume and also the monitoring of the pressure inside the infusion line from the drug reservoir to the pump and from the pump to the patient body.

The measuring element or sensor generates an analog signal based on the pressure wave inside the infusion line. The signal is conditioned and transmitted to a measuring system which measures its peak value and zero level—parameters characterizing a single cycle of the pump operation. The zero level represents the static pressure measured when the pump is idle, and the peak value represents the pressure when the pump is operating. The measured parameters are transmitted via an analog-to-digital converter to an analyzing system which compares the measured parameters with preset values.

The device of the present invention simultaneously controls the volume of each single stroke of the pump and indicates many possible alarm states of a delivery system. In the first case, the device can operate as an open loop or a closed loop, i.e., if the device detects a quantitative deviation in the volume of a single stroke of the pump, it can signal an alarm state or can automatically correct the operation of the pump by increasing or decreasing the frequency of the pump cycles. In the second case, the device operates only as an open loop, i.e., if the device detects an alarm state, the alarm is set on and the pump operation is stopped.

In addition, the device of the present invention provides continuous monitoring of a drug delivery system, i.e., the device operates during each cycle of the pump.

The device of the present invention is described below by reference to FIG. 1 which is a block diagram of a device for monitoring the operation of a drug delivery system, comprising a pump 6 which is controlled to deliver a liquid from a reservoir 7 through a catheter 8 provided with a hypodermic needle 9.

When the embodiment of the device illustrated in the drawing is used, a control signal from a control and analyzing system 5 activates the operation of the pump. Displacement of the fluid by the pump causes an overpressure in the pump section. The overpressure decreases when a cycle of the pump is completed.

A measuring element or sensor 1 located in the infusion line generates an analog signal based on the pressure course. The signal is transmitted by a matching system 2 which conditions the signal to enable a measuring system 3 to measure its zero level and peak value. The measured parameters are transmitted to an analog-to-digital converter 4 and then analyzed in the control and analyzing system 5.

It has been found that the amplitude of the signal, calculated as the difference between the peak value and zero level, depends on the pressure and/or the single stroke volume of the pump delivery. This dependence may be linear.

The device of the present invention achieves continuous quantitative control or monitoring of the actual delivery of the pump by continuously comparing the measured value of the signal amplitude calculated by the control and analyzing system 5 to the reference value recorded in the memory of the control and analyzing system 5. Since the volume intended to be delivered by each pumping cycle is constant, the amplitude of the pressure signal should also be constant under constant conditions.

If a discrepancy in the single stroke volume is detected, an alarm state can be set on or the pump operation can be corrected automatically, i.e., the control and analyzing system 5 can stop the operation of the pump or can automatically correct the operation of the pump by increasing or decreasing the frequency of the pump cycles. This is worthy of note since the device of the present invention can therefore provide feedback that can be used to control insulin infusions.

The signal from the measuring element or sensor can also simultaneously monitor the pressure inside the infusion line from the drug reservoir to the pump and from the pump to the patient. The result of that measurement can be used as an indicator of many alarm states. These include: Supply voltage drop, positive or negative external pressure influence, outlet catheter blockage, breakage of the catheter or disconnection of the catheter from the patient, blockage of the connector between the drug reservoir and the pump as well as the appearance of an air bubble in the pump mechanism.

This is possible due to changes in the measured values of the parameters when any of the above malfunctions occurs. The device of the present invention can detect alarm states by comparing the measured values of the signal, i.e., the zero level, peak value and/or signal amplitude, to the respective reference values recorded in the memory of the control and analyzing system 5. After detecting an alarm state, the device of the present invention can differentiate between alarm states by recording the measurements, comparing them with subsequently measured values and analyzing the character of change in the measured values of the parameters.

Examples of changes in the measured values of the parameters when a disturbance occurs are given in Table I.

TABLE I

| Disturbance | Most Sensitive Symptoms Caused by the Disturbance | Alarm State |
|---|---|---|
| Battery voltage drop | Peak value drop | I |
| Decrease in the stroke volume | Peak value drop | I |
| Air bubble inside pump mechanism | Peak value large drop | II |
| Blockage of the connector between reservoir and pump | Peak value large drop | II |
| Increase in the stroke volume | Peak value rise | III |
| Influence of an external negative hydrostatic pressure | Zero level drop | IV |
| Influence of an external positive hydrostatic pressure | Zero level rise | V |
| Catheter cracks | Zero level rise | V |
| Disconnection of the catheter from the body | Zero level rise | V |
| Blockage of the catheter | Zero level large rise | VI |

The alarm states indicated by Roman numerals are not exclusive.

The occurrence of any of the disturbances mentioned above causes the signal parameters to pass the upper or lower values of the preset limits and switches the device into one or more of the alarm states.

The above mentioned operation of the device of the present invention ensures that activation of the pump actually results in a preset volume of a drug passing through the catheter to the patient body.

In summary, the device of the present invention has the following advantages:

(1) it can monitor the actual delivery volume of the pump at the outlet of the catheter and operate as a feedback control of the delivery of the pump; and (2) it can monitor the proper operation of a drug delivery system by indication of many alarm states.

The present invention is also directed to a drug delivery system comprising the device and a method for monitoring the operation of a drug delivery system comprising using the device.

Although the device and the method of use thereof according to the present invention were developed primarily with a view to the administration of insulin to diabetic patients, the device and method are also useful in the administration of other dissolved drugs which advantageously are administered over a prolonged period of time. Examples of such drugs are heparin, oxytocin, human growth hormone and cancer chemotherapeutics.

What has been indicated in the specification in a concrete or specific way relating to the present invention is given as examples only and should in no way be considered as limiting—in one or more respects—the scope of the present invention. Many modifications, changes or replacements may be made without exceeding the scope of the present invention wholly or in part or without departing from the spirit or the idea of the present invention wholly or in part.

We claim:

1. A device for monitoring the operation of a drug delivery system comprising:
   (a) a volumetric micropump which delivers in the form of a single stroke a preset amount of a drug from a drug reservoir through a catheter to a patient body;
   (b) a measuring element or sensor located in the infusion line which generates an analog signal based on the actual pressure or the single stroke volume of the micropump;
   (c) a matching system which conditions the signal produced by the measuring element or sensor and transmits the signal to a measuring system which measures the peak value and zero level of the signal and transmits the measured parameters to an analog-to-digital converter; and
   (d) an analyzing and control system which compares the measured parameters and the calculated amplitude with preset values recorded in the memory of the analyzing and control system and which (i) signals an alarm state or automatically corrects the operation of the micropump if a quantitative deviation in the volume of a single stroke of the pump is detected and (ii) signals an alarm state if another alarm state of the drug delivery system is detected.

2. The device according to claim 1, wherein the device differentiates between alarm states by recording the measured parameters, comparing the measured parameters with subsequently measured values and analyzing the character of change in the measured parameters.

3. The device according to claim 1, wherein the device operates during each cycle of the micropump.

4. The device according to claim 1, wherein the drug is insulin.

5. A device for monitoring the operation of a drug delivery system which comprises:
   (a) a volumetric micropump which delivers in the form of a single stroke a preset amount of a drug from a drug reservoir through a catheter to a patient body;
   (b) a measuring element or sensor located in the infusion line which generates an analog signal based on the actual pressure or the single stroke volume of the micropump;
   (c) a matching system which conditions the signal produced by the measuring element or sensor and transmits the signal to a measuring system which measures the peak value and zero level of the signal and transmits the measured parameters to an analog-to-digital converter; and
   (d) an analyzing and control system which compares the calculated amplitude with a preset value recorded in the memory of the analyzing and control system and which signals an alarm state or automatically corrects the operation of the micropump if a quantitative deviation in the volume of a single stroke of the pump is detected.

6. A device for monitoring the operation of a drug delivery system which comprises:
   (a) a volumetric micropump which delivers in the form of a single stroke a preset amount of a drug from a drug reservoir through a catheter to a patient body;
   (b) a measuring element or sensor located in the infusion line which generates an analog signal based on the actual pressure or the single stroke volume of the micropump;
   (c) a matching system which conditions the signal produced by the measuring element or sensor and transmits the signal to a measuring system which measures the peak value and zero level of the signal and transmits the measured parameters to an analog-to-digital converter; and
   (d) an analyzing and control system which compares the measured parameters and the calculated amplitude with preset values recorded in the memory of the analyzing and control system and which signals an alarm state if one of many alarm states of the drug delivery system is detected.

7. A drug delivery system comprising the device of claim 1.

8. A method for monitoring the operation of a drug delivery system comprising using the device of claim 1.

* * * * *